US00PP30367P2

(12) United States Plant Patent
Graff

(10) Patent No.: US PP30,367 P2
(45) Date of Patent: Apr. 9, 2019

(54) POINSETTIA PLANT NAMED 'Q102'

(50) Latin Name: ***Euphorbia pulcherrima* Willd.**
Varietal Denomination: Q102

(71) Applicant: Poul Graff, Sabro (DK)

(72) Inventor: Poul Graff, Sabro (DK)

(73) Assignee: Graff Breeding A.S., Sabro (DK)

( * ) Notice: Subject to any disclaimer, the term of this patent is extended or adjusted under 35 U.S.C. 154(b) by 0 days.

(21) Appl. No.: 15/932,701

(22) Filed: Apr. 10, 2018

(51) Int. Cl.
*A01H 5/02* (2018.01)

(52) U.S. Cl.
USPC ..... Plt./303
CPC ..... *A01H 5/02* (2013.01)

(58) Field of Classification Search
USPC ..... Plt./303, 307
CPC ..... A01H 5/02
See application file for complete search history.

*Primary Examiner* — Kent L Bell
(74) *Attorney, Agent, or Firm* — C. A. Whealy

(57) ABSTRACT

A new and distinct cultivar of *Poinsettia* plant named 'Q102', characterized by its compact, upright and uniformly mounding plant habit; moderately vigorous growth habit; freely branching habit; dark green-colored leaves; large and full inflorescences with numerous light red purple to light red-colored flower bracts; and excellent post-production longevity.

2 Drawing Sheets

Botanical designation: *Euphorbia pulcherrima* Willd.
Cultivar denomination: 'Q102'.

BACKGROUND OF THE INVENTION

The present invention relates to a new and distinct cultivar of *Poinsettia* plant, botanically known as *Euphorbia pulcherrima* Willd. and hereinafter referred to by the name 'Q102'.

The new *Poinsettia* plant is a product of a planned breeding program conducted by the Inventor in Sabro, Denmark. The objective of the breeding program is to create uniform and freely-branching *Poinsettia* plants with attractive inflorescences and good postproduction longevity.

The new *Poinsettia* plant originated from a cross-pollination made by the Inventor in January, 2015 in Sabro, Denmark of a proprietary selection of *Euphorbia pulcherrima* Willd. identified as code number 2012-0601, not patented, as the female, or seed, parent with a proprietary selection of *Euphorbia pulcherrima* Willd. identified as code number 2012-0107, not patented, as the male, or pollen, parent. The new *Poinsettia* plant was discovered and selected by the Inventor as a single flowering plant within the progeny of the stated cross-pollination in a controlled greenhouse environment in Sabro, Denmark in October, 2016.

Asexual reproduction of the new *Poinsettia* plant by terminal vegetative cuttings in a controlled greenhouse environment in Sabro, Denmark since May, 2017 has shown that the unique features of this new *Poinsettia* plant are stable and reproduced true to type in successive generations of asexual reproduction.

SUMMARY OF THE INVENTION

Plants of the new *Poinsettia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'Q102'. These characteristics in combination distinguish 'Q102' as a new and distinct *Poinsettia* plant:

1. Compact, upright and uniformly mounding plant habit.
2. Moderately vigorous growth habit.
3. Freely branching habit.
4. Dark green-colored leaves.
5. Large and full inflorescences with numerous light red purple to light red-colored flower bracts.
6. Excellent post-production longevity.

Plants of the new *Poinsettia* can be compared to plants of the female parent selection. In side-by-side comparisons, plants of the new *Poinsettia* differ primarily from plants of the female parent selection in flower bract color as flower bracts of plants of the female parent selection are salmon pink in color.

Plants of the new *Poinsettia* can be compared to plants of the male parent selection. In side-by-side comparisons, plants of the new *Poinsettia* differ primarily from plants of the male parent selection in flower bract color as flower bracts of plants of the male parent selection are red in color.

Plants of the new *Poinsettia* can also be compared to plants of *Euphorbia pulcherrima* Willd. 'NPCW10164', disclosed in U.S. Plant Pat. No. 22,597. In side-by-side comparisons, plants of the new *Poinsettia* differ primarily from plants of 'NPCW10164' in the following characteristics:

1. Plants of the new *Poinsettia* are more freely branching than plants of 'NPCW10164'.
2. Flower bracts of plants of the new *Poinsettia* are slightly shorter than flower bracts of plants of 'NPCW10164'.

3. Flower bracts of plants of the new *Poinsettia* are lighter red in color than flower bracts of plants of 'NPCW10164'.

BRIEF DESCRIPTION OF THE PHOTOGRAPHS

The accompanying photographs illustrate the overall appearance of the new *Poinsettia* plant showing the colors as true as it is reasonably possible to obtain in colored reproductions of this type. Colors in the photographs may differ slightly from the color values cited in the detailed botanical description which accurately describe the colors of the new *Poinsettia* plant.

The photograph on the first sheet is a side perspective view of a typical flowering plant of 'Q102' grown in a container.

The photograph at the top of second sheet is a close-up view of a typical dissected inflorescence of 'Q102'.

The photograph at the bottom of second sheet is a close-up view of the lower and upper surfaces of typical leaves of 'Q102'.

DETAILED BOTANICAL DESCRIPTION

The aforementioned photographs and following observations, measurements and values describe plants grown during the winter in 13-cm containers in a glass-covered greenhouse in Sabro, Denmark and under cultural practices typical of commercial *Poinsettia* production. During the production of the plants, day temperatures ranged from 20° C. to 25° C., night temperatures ranged from 19° C. to 21° C. and light levels ranged from 40 to 50 klux. Plants were pinched one time eight weeks after planting and plants were 20 weeks old when the photographs and the description were taken. In the description, color references are made to The Royal Horticultural Society Colour Chart, 2001 Edition, except where general terms of ordinary dictionary significance are used.

Botanical classification: *Euphorbia pulcherrima* Willd. 'Q102'.

Parentage:

*Female, or seed, parent*.—Proprietary selection of *Euphorbia pulcherrima* Willd. identified as code number 2012-0601, not patented.

*Male, or pollen, parent*.—Proprietary selection of *Euphorbia pulcherrima* Willd. identified as code number 2012-0107, not patented.

Propagation:

*Type*.—Terminal vegetative cuttings.

*Time to initiate roots, summer*.—About three weeks at temperatures about 24° C.

*Time to initiate roots, winter*.—About four weeks at temperatures about 24° C.

*Time to produce a rooted young plant, summer*.—About eight weeks at temperatures about 24° C.

*Time to produce a rooted young plant, winter*.—About ten weeks at temperatures about 24° C.

*Root description*.—Medium in thickness, fleshy; color, close to 161D, actual color of the roots is dependent on substrate composition, water quality, fertilizer type and formulation, substrate temperature and physiological age of roots.

*Rooting habit*.—Freely branching; dense.

Plant description:

*Plant and growth habit*.—Compact, upright and uniformly mounded plant habit; inverted triangle with rounded crown; large full inflorescences positioned above the foliar plane; moderately vigorous growth habit and moderate growth rate.

*Plant height, soil level to top of foliar plane*.—About 20 cm to 40 cm.

*Plant height, soil level to top of floral plane*.—About 20 cm to 40 cm.

*Plant diameter or spread*.—About 30 cm to 50 cm.

*Lateral branch description*.—Branching habit: Freely branching habit, about three to six lateral branches develop after pinching. Length: About 15 cm to 25 cm. Diameter: About 3 mm to 6 mm. Internode length: About 1 cm to 5 cm. Strength: Strong. Texture and luster: Smooth, glabrous; semi-glossy. Angle: Mostly upright. Color, developing: Close to 138A. Color, developed: Close to 137A; at the internodes, close to 137C.

*Leaf description*.—Arrangement and appearance: Alternate, simple. Length: About 8 cm to 13 cm. Width: About 7 cm to 10 cm. Shape: Broadly ovate. Apex: Acute. Base: Truncate. Margin: Entire, shallowly to medium lobed. Venation pattern: Pinnate. Aspect: Mostly flat. Texture and luster, upper and lower surfaces: Rugose, glabrous; leathery; matte. Color: Developing leaves, upper surface: Close to 137B. Developing leaves, lower surface: Close to 138A. Fully expanded leaves, upper surface: Close to N189A; venation, close to 139A. Fully expanded leaves, lower surface: Close to N138B; venation, close to 147C. Petioles: Length: About 5 mm to 10 mm. Diameter: About 3 mm to 5 mm. Texture and luster, upper and lower surfaces: Smooth, glabrous; semi-glossy. Color, upper and lower surfaces: Close to 138B.

Inflorescence description:

*Inflorescence type and habit*.—Large full inflorescences are compound corymbs of cyathia with light red purple to light red-colored flower bracts subtending the cyathia; one inflorescence per lateral branch with inflorescences positioned above and beyond the foliar plane.

*Fragrance*.—None detected.

*Natural flowering season*.—Plants flower naturally during the autumn and winter under long nyctoperiod conditions; inflorescence initiation and development can be induced under artificial long nyctoperiod conditions; medium flowering habit, response time is about nine to ten weeks after start of long nyctoperiod conditions.

*Post-production longevity*.—Excellent post-production longevity; plants of the new *Poinsettia* maintain good substance and bract color for about eight to ten weeks under interior conditions; flower bracts persistent.

*Inflorescence diameter*.—About 13 cm to 18 cm.

*Inflorescence height*.—About 5 cm to 7 cm.

*Flower bracts*.—Quantity per inflorescence: About 20 to 25. Length: About 9 cm to 11 cm. Width: About 6 cm to 8 cm. Shape: Ovate. Apex: Cuspidate to acute. Base: Obtuse. Margin: Entire, shallowly lobed. Venation: Pinnate. Texture and luster, upper and lower surfaces: Rugose, glabrous; velvety; matte. Aspect: Mostly horizontal to slightly downward. Color: Developing (transitional) bracts, upper and lower surfaces: Variable sectors, close to 49D and 144A. Fully expanded bracts, upper surface: Close to N57D becoming closer to 51A; color becoming closer to 51B with development. Fully expanded bracts, lower surface: Close to 49C becoming closer to 48C; color becoming closer to 51D with development. Flower bract petioles: Length: About 5 mm to 10 mm. Diameter: About 3 mm to 5 mm. Texture, upper and lower surfaces: Smooth, glabrous. Color, upper and lower surfaces: Close to 144B.

*Cyathia*.—Quantity per corymb: About 10 to 20. Length: About 4 mm. Width: About 4 mm. Shape: Rounded. Color, developing, inner surface: Close to 138D. Color, developing, outer surface: Close to 138B. Color, fully developed, inner surface: Close to 138C. Color, fully developed, outer surface: Close to 138B. Nectaries: Quantity per cyathium: Typically one. Length: About 3 mm to 4 mm. Diameter: About 2 mm to 5 mm. Shape: Lanceolate. Texture, inner and outer surfaces: Smooth, glabrous. Color, developing, inner and outer surfaces: Close to 146C. Color, fully developed, inner surface: Close to 5C. Color, fully developed, outer surface: Close to 5A.

*Peduncles*.—Length: About 2 mm to 5 mm. Diameter: About 2 mm to 5 mm. Strength: Strong. Texture and luster: Smooth, glabrous; semi-glossy. Angle: Mostly upright. Color: Close to 139C.

*Reproductive organs*.—Stamens: Quantity per cyathium: About 50. Filament length: About 1 mm to 5 mm. Filament color: Close to N199B. Anther shape: Reniform. Anther length: About 1 mm. Anther color: Close to 20A. Amount of pollen: Moderate. Pollen color: Close to 14A. Pistils: Quantity per cyathium: Typically one. Pistil length: About 2 mm to 3 mm. Style length: About 1 mm to 2 mm. Style color: Close to 147D. Stigma diameter: About 3 mm. Stigma shape: Five-parted. Stigma color: Close to N34A. Ovary color: Close to 143A. Seeds and fruits: Seed and fruit production has not been observed on plants of the new *Poinsettia* to date.

Disease & pest resistance: To date, plants of the new *Poinsettia* have not been shown to be resistant to pathogens and pests common to *Poinsettia* plants.

Temperature tolerance: Plants of the new *Poinsettia* have been observed to tolerate temperatures ranging from about 12° C. to about 35° C.

It is claimed:

1. A new and distinct *Poinsettia* plant named 'Q102' as illustrated and described.

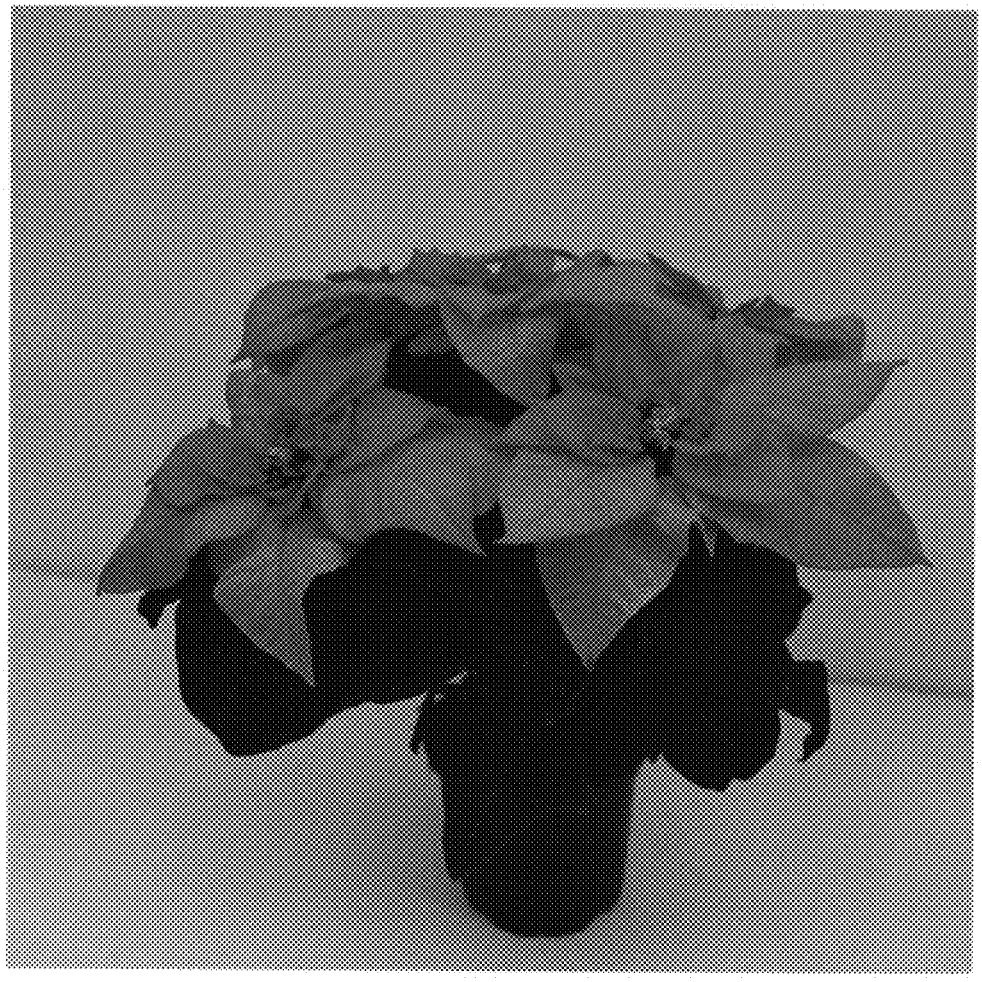

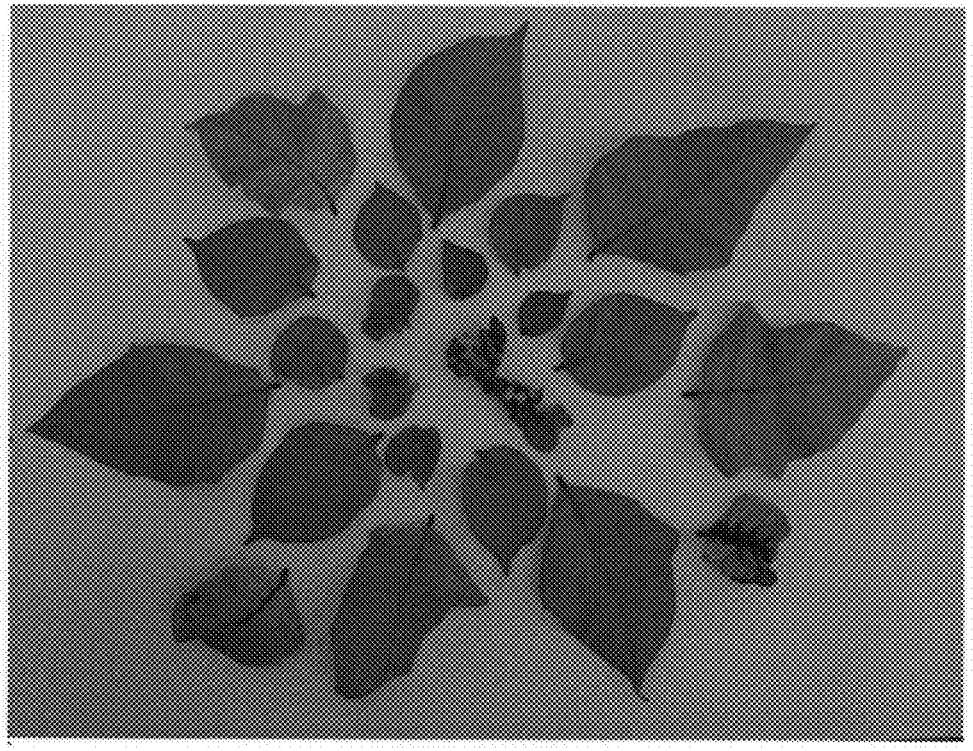
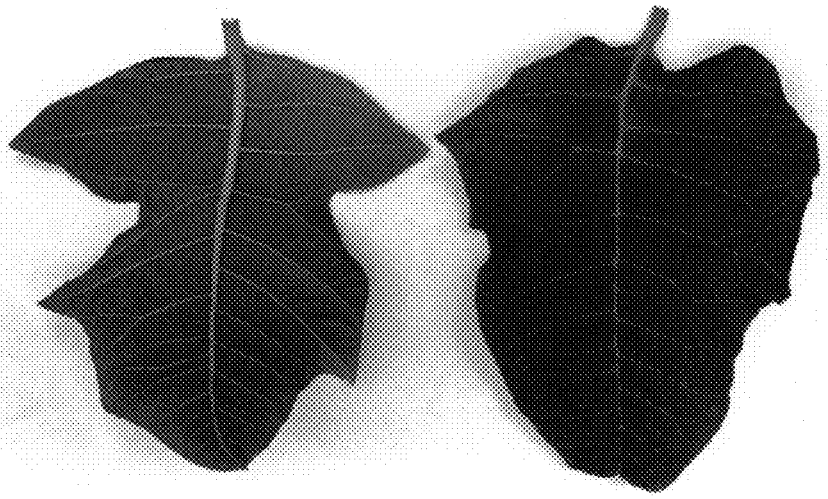

* * * * *